United States Patent [19]

Hamel et al.

[11] Patent Number: 4,662,880
[45] Date of Patent: May 5, 1987

[54] PSEUDOEPHEDRINE, BROMPHENIRAMINE THERAPY

[75] Inventors: L. G. Hamel, Sunnyvale; Felix A. Landrau, Milpitas; Patrick S.L. Wong, Hayward; George V. Guittard, Cupertino, all of Calif.

[73] Assignee: Alza Corporation, Palo Alto, Calif.

[21] Appl. No.: 839,384

[22] Filed: Mar. 14, 1986

[51] Int. Cl.⁴ ............................................. A61K 9/22
[52] U.S. Cl. .................................... 604/892; 514/357; 514/962; 424/473
[58] Field of Search ............................. 604/890–894; 424/16, 14, 19, 22, 15

[56] References Cited

U.S. PATENT DOCUMENTS

| | | | |
|---|---|---|---|
| 4,369,172 | 1/1983 | Schor et al. | 424/22 |
| 4,449,983 | 5/1984 | Cortese et al. | 604/892 |
| 4,457,907 | 7/1984 | Porter | 424/16 |
| 4,552,899 | 11/1985 | Sunshine et al. | 514/653 |
| 4,576,604 | 3/1986 | Guittard et al. | 604/890 |
| 4,609,374 | 9/1986 | Ayer | 604/892 |
| 4,612,008 | 9/1986 | Wong et al. | 604/891 |

Primary Examiner—C. Fred Rosenbaum
Assistant Examiner—Jerome R. Smith, Jr.
Attorney, Agent, or Firm—Paul L. Sabatine; Edward L. Mandell; Steven F. Stone

[57] ABSTRACT

A dosage form is disclosed for delivering the beneficial drugs pseudoephedrine and brompheniramine to a biological environment of use.

14 Claims, 2 Drawing Figures

PSEUDOEPHEDRINE, BROMPHENIRAMINE THERAPY

FIELD OF THE INVENTION

This invention pertains to both a beneficial composition comprising the drug pseudoephedrine and brompheniramine, and to a delivery system for administering the composition comprising the drugs to a recipient.

BACKGROUND OF THE INVENTION

Antihistamine and decongestants are used for the temporary relief of symptoms of the common cold, allergic rhinitis and sinusitis. The antihistamine brompheniramine and the decongestant pseudoephedrine are therapeutically indicated for recipients needing relief of these symptoms.

Brompheniramine is a propylamine derivative antihistamine. Brompheniramine is a racemic mixture of the dextro and levo isomers. Pharmacologic activity is predominantly due to the d-isomer. Dextrobrompheniramine, the dextro isomer, is approximately twice as active. Brompheniramine is administered for its effects as a therapeutically acceptable salt, preferably as brompheniramine maleate. Brompheniramine maleate occurs as a white crystalline powder, freely soluble in aqueous-type fluids, and it is absorbed from the gastrointestinal tract.

Pseudoephedrine is a sympathomimetic drug which occurs naturally in plants of the Ephedra. Pseudoephedrine is a stereoisomer of ephedrine. Pseudoephedrine is administered for its beneficial effects as a therapeutically acceptable salt, preferably as the hydrochloride or the sulfate. Pseudoephedrine hydrochloride occurs as a fine, white crystal or powder, it is very soluble in aqueous-type fluids, and it is absorbed from the gastrointestinal tract.

It would be desirable to provide a pharmaceutical dosage form comprising the two different drugs that are initially delivered in a therapeutically effective amount, followed by delivery of the drugs at a controlled rate, and for a time period, established to meet a specific therapeutic need. That is, it would be desirable to provide a dosage form that comprises an exterior lamina comprising pseudoephedrine and brompheniramine and a releasable binder, which lamina delivers both drugs immediately for substantially eliminating the start-up time of the dosage form and for providing immediate therapy to a recipient. The exterior drug-containing lamina for delivering an initial drug-pulse acts in cooperation with the dosage form that follows with the drugs then delivered at a controlled rate over time.

Additionally, it would be desirable to provide a pharmaceutical dosage form comprising the two different drugs for their simultaneous administration for obtaining the physiological and pharmacological benefits of each drug. Such a novel dosage form can be used for the desired medical relief where each individual drug addresses different symptoms of the particular medical situation. Prior to this invention, however, the coadministration of these drugs in a predetermined ratio did not appear feasible. For example, pseudoephedrine and brompheniramine appear kinetically incompatible in a pharmaceutical osmotically-controlled dosage form for their respective administrations within prescribed ratios because of their individual osmotic properties and their solubilities. Additionally, it is unobvious from their pharmacokinetic properties that pseudoephedrine and brompheniramine can be coadministered from a dosage form to the body at rates that are individually selected to achieve each of their separate therapeutic plasma concentrations.

Thus, in the light of the above presentation, it will be appreciated by those versed in the dispensing art, that if a novel and unique dosage form is made available for first, administering a pulsed amount of pseudoephedrine and brompheniramine and secondly, making available a means for housing the pseudophedrine and brompheniramine for their administration at a controlled and continuous rate in therapeutically effective ratios for obtaining the benefits of each drug, such a dosage form would have a definite use and be a valuable contribution to the dispensing art.

OBJECTS OF THE INVENTION

Accordingly, it is an immediate object of this invention to provide a composition comprising pseudoephedrine and brompheniramine that can be administered to biological receptor sites to produce the desired pharmacokinetic effects.

Another object of the invention is to provide a dosage form that can dispense pseudoephedrine and brompheniramine in a preselected ratio and at controlled rates for obtaining the pharmacological and the physiological benefit of each drug, and which dosage form thusly represents an improvement and advancement in therapy.

Another object of the invention is to provide an osmotic system manufactured in the form of an osmotic device that comprises an exterior lamina composition comprising pseudoephedrine and brompheniramine and a releasable binder that delivers the drugs immediately for increasing the period of time pseudoephedrine and brompheniramine are available for performing their beneficial effects, followed by prolonged release of the drugs from the interior of the osmotic device.

Another object of the invention is to provide an osmotic system adapted for administering pseudoephedrine and brompheniramine to a warm-blooded animal from an lamina comprising pseudoephedrine and brompheniramine for delivering an initial pulse of these drugs which acts in cooperation with the osmotic system that follows with delivery of pseudoephedrine and brompheniramine at a rate controlled by the osmotic system.

Another object of the invention is to provide an osmotically-controlled dosage form that can house pseudoephedrine and brompheniramine and can codispense the two drugs to their biological drug receptors for their separate therapeutic activities over a prolonged period of time.

Another object of the invention is to provide an osmotic device comprising a single compartment containing a composition comprising a member selected from the group consisting of pseudoephedrine and its therapeutically acceptable salts and brompheniramine and its therapeutically acceptable salts, and which osmotic device can simultaneously administer the pseudoephedrine and the brompheniramine at a preselected prescribed ratio for providing a complete pharmaceutical regimen for the two drugs to a warm-blooded animal.

Another object of the invention is to provide a complete pharmaceutical regimen for a composition comprising a pseudoephedrine and a brompheniramine with the pharmacological parameters of the composition more favorable than those of the drugs alone, and which composition can be dispensed from an osmotic delivery system; the use of which requires intervention only for initiation and possibly termination of the regimen.

Another object of the invention is to provide an osmotic device for dispensing pseudoephedrine and brompheniramine, which osmotic device comprises a wall member whose fluid permeability increases over a prolonged period of time.

Another object of the present invention is to provide an osmotic therapeutic system comprising pseudoephedrine and brompheniramine that are codelivered at a mass ratio concomitantly with the system exhibiting increased permeability that is gradual over time.

Other objects, features and advantages of the invention will be more apparent to those versed in the art from the following specification, taken in conjunction with the drawings and the accompanying claims.

BRIEF DESCRIPTION OF THE DRAWINGS

In the drawing figures, which are not drawn to scale, but are set forth to illustrate various embodiments of the invention, the drawing figures are as follows.

In the drawings and in the specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
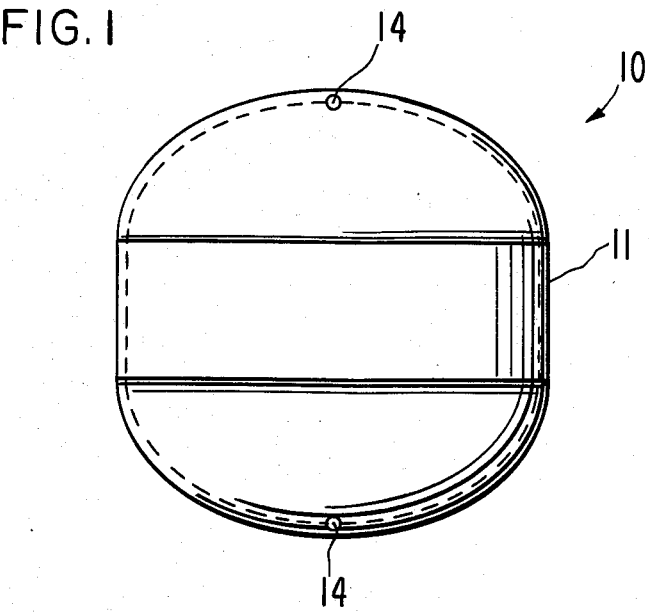
FIG. 1 is a view of an osmotic device designed and shaped for orally administering the two beneficial drugs pseudoephedrine and brompheniramine to the gastrointestinal tract; and, FIG. 2 is an opened view of the osmotic device of FIG. 1 illustrating the structure of the osmotic device.
Figure 2:
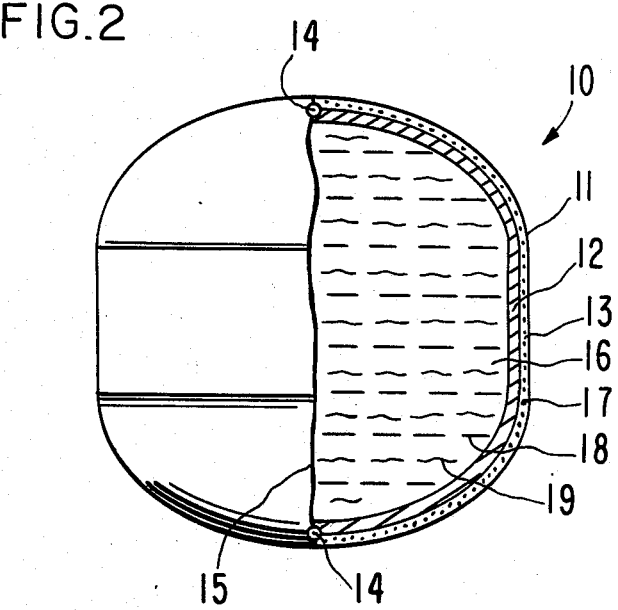

Turning now to the drawing figures in detail, which drawing figures are an example of the dosage form provided by the invention, and which example is not to be considered as limiting, one example is the osmotic dosage form illustrated in FIGS. 1 and 2 and designated by the numeral 10. In FIG. 1, osmotic dosage form 10 comprises a body member 11 comprising a wall 12 illustrated in a continuous dashed line, that surrounds and forms an internal compartment not seen in FIG. 1. Device 10 further comprises an exterior lamina 13 and at least one exit means 14 for connecting the interior of dosage form 10 with the exterior environment of use.

In FIG. 2, osmotic dosage form 10 is seen in opened view with wall 12 sectioned at 15. In FIG. 2, osmotic dosage form 10 comprises body 11, wall 12 that surrounds and defines internal compartment 16 and exterior lamina 13. Exterior lamina 13 is initially supported on at least a part, or all of the exterior surface of wall 12. Wall 12 comprises at least one exit means 14, or more than one exit means 14 for dispensing the contents of compartment 16 from dosage form 10.

Wall 12 of dosage form 10 comprises a composition that is permeable to the passage of an exterior fluid present in the environment of use, and it is substantially impermeable to the passage of drug and other ingredients present in compartment 16. Semipermeable wall 12 of device 10 is substantially inert, and it maintains its physical and chemical integrity during the drug dispensing life of dosage form 10. The phrase "keeps its physical and chemical integrity" means wall 12 does not lose its structure and it does not change during the dispensing life of dosage form 10. Wall 12 is formed of a composition comprising cellulose triacetate and hydroxypropyl cellulose. Wall 12 comprises a composition containing from 70 to 85 weight percent cellulose triacetate, and from 15 to 30 weight percent hydroxypropylcellulose, with the total weight percent equal to 100. Wall 12, in one presently preferred embodiment comprises 75 weight percent cellulose triacetate and 25 weight percent hydroxypropylcellulose. In another preferred embodiment, wall 12 comprises 80 weight percent cellulose triacetate and 20 weight percent hydroxypropylcellulose. The acetyl content of the cellulose triacetate can be from 39.8% to 43.5%. Wall 12 exhibits an increased permeability to the passage of fluid over time attributed to the presence of hydroxypropylcellulose in wall 12. This unique property of wall 12, acting in cooperation with dosage form 10, enables dosage form 10 to deliver greater than 90% to 95% of its drug content over a prolonged period of 24 hours.

Dosage form 10, manufactured in the form of an osmotic device comprises a lamina 13 coated onto the exterior surface of wall 12. Lamina 13 comprises a composition 17, represented by dots, which composition comprises the drugs pseudoephedrine and brompheniramine, and an aqueous soluble carrier hydroxypropylmethylcellulose. Lamina 13 comprising composition 17 provides for making available instantly the drugs pseudoephedrine and brompheniramine, preferably as their pharmaceutically acceptable salt. In operation, when device 10 is in a fluid environment of use, lamina 13 dissolves or undergoes dissolution and concurrently delivers composition 17 to the drug receptors. Lamina 13 containing drug composition 17, by providing immediate drug delivery, essentially overcomes the time required for the drugs to be delivered from compartment 16 of device 10. A start-up time is needed for imbibing fluid through wall 12 for device 10 to hydrodynamically dispense the components of compartment 16 through exit passageway 14 to the environment of use. Lamina 13, in one presently preferred embodiment is formed of a composition comprising pseudoephedrine 55 to 65 mg, brompheniramine 5 to 8 mg and hydroxypropylmethylcellulose up to 100 mg. In another preferred embodiment lamina 13 comprises pseudoephedrine 25 to 35 mg, brompheniramine 2 to 5 mg and hydroxypropylmethylcellulose up to 100 mg. More specifically, lamina 13 in one embodiment comprises 60 mg of pseudoephedrine, 6 mg of brompheniramine and 34 mg of hydroxypropylmethylcellulose; in another embodiment 30 mg of pseudoephedrine, 3 mg of brompheniramine maleate and 67 mg of hydroxypropylmethylcellulose; in another embodiment lamina 13 comprises 60 mg of pseudoephedrine, 6 mg of brompheniramine and 17 mg of hydroxypropylmethylcellulose; and in another embodiment 30 mg of pseudoephedrine, 3 mg of brompheniramine and 8 mg of hydroxypropylmethylcellulose. Lamina 13 begins to release the drug pair instantly in the fluid environment of use, and it completely releases all of the drug pair during the first thirty minutes. This instant release thereby provides the drug pair for immediate passage into the plasma of a recipient.

Internal compartment 16 houses a dispensable composition comprising the beneficial drugs pseudoephedrine 18, identified by dashes, and beneficial drug brompheniramine 19, identified by wavy lines. The two drugs are present in compartment 16 in a fixed ratio and they are dispensed at a rate of release essentially equal to the ratios at which drug 18 and drug 19 were formulated into compartment 16. The release rate ratio, essentially equal to their compartment ratio, is both unobvious and unexpected based on thermodynamic physics. Thermodynamics indicates the two drugs would be released at their equilibrium solubility ratios, for example, in an embodiment comprising pseudoephedrine hydrochloride and brompheniramine maleate at a ratio of 1.75:1. While device 10 in operation codelivered pseudoephedrine hydrochloride and brompheniramine maleate as their mass ratio of 15:1. This release rate ratio is the same ratio the two drugs were formulated into compartment 16. According to thermodynamic equilibrium equations applicable to an osmotic dosage form for co-delivering pseudoephedrine hydrochloride, identified as drug A, and brompheniramine maleate, identified as drug B, the equations are as follows:

$$S_T = S_A + S_B \qquad (1)$$

wherein $S_T$ is the total solubility of drug A and drug B in fluid imbibed into compartment 16; $S_A$ is the solubility of drug A in the fluid, and $S_B$ is the solubility of drug B in the fluid; the release rate $RR_A$ for drug A is given by equation (2):

$$RR_A = (k/h) A \Delta \pi S_A \qquad (2)$$

wherein $S_A$ is the solubility of drug A in fluid in the compartment, k is the permeability of wall 12 to aqueous-type fluids present in the environment of use, h is the thickness of wall 12, $\Delta\pi$ is the total osmotic pressure gradient of the drug formulation across wall 12 against an exterior fluid present in the environment of use, and A is the area of wall 12; and by equation (3) for the controlled release rate $RR_B$ for drug B as follows:

$$RR_B = (k/h) A \Delta \pi S_B \qquad (3)$$

wherein $S_B$ is the solubility of drug B in the presence of fluid imbibed through wall 12 into compartment 16, k is the permeability of wall 12 to the fluid present in the environment, h is the thickness of wall 12, $\Delta\pi$ is the total osmotic pressure gradient of the drug formulation across wall 12 against fluid present in the environment of use, and A is the area of wall 12; then, combining equations (2) and (3) the equilibrium solubility ratio SR for drug A exemplified by pseudoephedrine hydrochloride and for drug B exemplified by brompheniramine maleate is given by equations (4) and (5):

$$\frac{RR_A}{RR_B} = \frac{S_A}{S_B} = \frac{572 \text{ mg/ml}}{327 \text{ mg/ml}} \qquad (4)$$

$$SR = 1.75:1 \qquad (5)$$

Instead, the release rate ratios provided by this invention for drug A and drug B is given by equation (6) as follows:

$$\frac{RR_A}{RR_B} = \frac{C_A}{C_B} \qquad (6)$$

wherein $C_A$ is the concentration of drug A in compartment 16 at the initiation of the drug dispensing period, and $C_B$ is the concentration of drug B at the beginning of the drug dispensing period, then (7):

$$\frac{RR_A}{RR_B} = \frac{120}{8} \qquad (7)$$

$$RR_{A \cdot B} = 15:1$$

which two drugs, as determined by scientific measurements were coreleased in essentially the same ratio as their initial charge in compartment 16 at time zero. The ratio of the two drugs inside the compartment can be selected according to their therapeutic need. In this preselection, the controlled release rate for the codelivered drugs comprises essentially the same ratio as their mass ratio in the compartment. Generally, in one osmotic dosage form provided by the invention the compartment contains from 170 to 200 mg of pseudoephedrine and from 10 to 20 mg of brompheniramine, with more specific dosages comprising (a) 180 mg of pseudoephedrine hydrochloride and 18 mg of brompheniramine maleate; and (b) 180 mg of pseudoephedrine hydrochloride and 10 mg of brompheniramine maleate. In another osmotic dosage form provided by the invention, the compartment contains from 80 to 110 mg of pseudoephedrine and 3 to 8 mg of brompheniramine, with more specific dosage forms comprising (c) 90 mg of pseudoephedrine hydrochloride and 5 mg of brompheniramine maleate; and (d) 90 mg of pseudoephedrine hydrochloride and 3 mg of brompheniramine maleate. The preferred mass ratio is from 8:1 to 20:1 with a more specific mass ratio comprising 10:1 to 15:1 expressed as pseudoephedrine to brompheniramine. The compartment can contain also from 20 to 30 mg of sodium chloride, usually about 25 mg in a dosage form. The sodium chloride aids in codispensing a higher percent of the drugs delivered at zero-order, usually 15 hours and longer. The compartment can contain also hydroxypropylmethylcellulose as an aid for controlling the dissolution of the composition in the compartment.

The expression "exit means" as used herein comprises means and methods suitable for coreleasing the beneficial drugs pseudoephedrine and brompheniramine from the dispensing device. The means include at least one passageway or orifice that passes through wall 12 for communicating with the drugs in compartment 16. The expression "at least one passageway" includes aperture, orifice, bore, pore, porous element through which drugs can migrate, a hollow fiber, capillary tube, and the like. The expression includes also a material that erodes or is leached from wall 12 in the fluid environment of use to produce at least one passageway in the device. Representative materials suitable for forming at least one passageway, or a multiplicity of passageways, include an erodible poly(glycolic) or poly(lactic) acid member in the wall, a gelatinous filament, poly(vinyl alcohol), leachable materials such as fluid removable pore forming polysaccharides, salts, or oxides, and the like. A passageway or a plurality of passageways can be formed by leaching a material such as sorbitol from the wall. The passageway can have any shape, such as round, triangular, square, elliptical, irregular and the like. The device can be constructed with one or more passageways in spaced apart relation on more than a single surface of a dosage form. Passageways, and equipment for forming passageways are disclosed in U.S. Pat. Nos. 3,916,899; 4,063,064 and 4,088,864. Passageways formed by leaching are disclosed in U.S. Pat. No. 4,200,098.

The osmotic dosage form of the invention is manufactured by standard manufacturing techniques. For example, the compartment forming ingredients are formulated by the wet granulation technique using an organic cosolvent, such as isopropyl alcohol - methylene dichloride, 80/20 v/v (volume/volume) as the granulating fluid. The ingredients forming the compartment in one manufacture comprising pseudoephedrine hydrochloride, brompheniramine maleate, sodium chloride, hydroxypropylmethylcellulose, and microcrystalline cellulose, are individually passed through a 40 mesh screen and then thoroughly blended in a mixer. Next, poly(vinylpyrrolidone) is dissolved in a portion of the granulation fluid, the cosolvent described immediately above. Then, the poly(vinylpyrrolodine solution) is slowly added to the dry powder blend with continual mixing in the blender. The granulating fluid is added until a wet blend is achieved, generally about 400 cc of granulating fluid per kilogram of blend. The wet mass blend is then forced through a 20 mesh screen onto oven trays and dried for 18 to 24 hours at 50° C. The dried granules are then sized with a 20 mesh screen. Next, magnesium stearate and silicon dioxide are added to the dry, screened granular blend, and this blend passed through an 80 mesh screen. The granulation is then put into milling jars and mixed on a jar mill for 10 to 15 minutes.

In another process, the drugs pseudoephedrine and brompheniramine and other ingredients are blended in a fluid bed granulation. After the powders are dry blended, a granulation fluid comprising a solution of poly(vinyl pyrrolidone) in water, is sprayed onto the powders and dried in the granulator. This process granulates all of the ingredients together while adding the granulation solution. After the granules are dried, the lubricant magnesium stearate is added to the granulation.

The composition forming blend, in either of the above processes, is then tabletted using a 4-station Manesty ® tablet press. The speed of the press is set at 30 rpm and the maximum load set at 2 tons. Two dosage forms are tabletted using the press, one using a 9/32 inch (7.15 mm) round, standard concave punch, and the other using a ⅜ inch (7.15 mm) round, standard concave punch.

The wall of the osmotic dosage systems, and the exterior instant release lamina can be formed by one technique using the air suspension procedure. This procedure consists in suspending and tumbling the drug forming compartment in a current of air and a wall forming, or lamina forming composition until, in either operation the wall or the lamina is applied to the drug forming compartment. The air suspension procedure is well-suited for independently forming the wall or the lamina. The air suspension procedure is described in U.S. Pat. No. 2,799,241; in *J. Am. Pharm. Assoc.* Vol. 48, pages 451 to 459, 1959: and ibid. Vol. 49, pages 82 to 84, 1960. Osmotic dosage-forming system can also be coated with the wall forming composition with a Wurster ® air suspension coater, using a methylene dichloride/methanol cosolvent 80/20 V/V; using 2.5 to 4% solids. The Aeromatic ® air suspension coater using a methylene dichloride/methanol cosolvent 87/13 V/V also can be used for applying the wall or the lamina. Other wall and laminating techniques such as pan coating can be used for providing the dosage form. In the pan coating system, wall forming, or lamina forming compositions are deposited by successive spraying of the compositions on the drugs accompanied by tumbling in a rotating pan. A pan coater is used to produce a thicker wall or lamina. A larger volume of methanol can be used in a cosolvent to produce a thinner wall or lamina. Finally, the wall or lamina coated compartments are dried in a forced air oven at 50° C. for a week to free the dosage form of solvent. Generally, the wall formed by these techniques will have a thickness of 2 to 20 mils with a presently preferred thickness of 4 to 10 mils. The exterior lamina generally will have a thickness of 0.5 to 15 mils, usually 0.5 to 7.5 mils.

Exemplary solvent suitable for manufacturing the wall or the lamina include inert inorganic and organic solvents that do not adversely harm the wall, the lamina, and the final systems. The solvents broadly include members selected from the group consisting of alcohols, ketones, esters, ethers, aliphatic hydrocarbons, halogenated solvents, cycloaliphatic solvents, aromatic, heterocyclic, aqueous, and mixtures thereof.

Following the procedures of the invention a series of dosage forms were prepared for dispensing pseudoephedrine and brompheniramine. Representative dosage forms contained (1) a total of 240 mg of pseudoephedrine and 24 mg of brompheniramine with the drug distribution in the dosage form comprising 180 mg of pseudoephedrine and 18 mg of brompheniramine in the compartment and 60 mg of pseudoephedrine and 6 mg of brompheniramine in the lamina; (2) a total of 240 mg of pseudoephedrine and 16 mg of brompheniramine distributed as 180 mg of pseudoephedrine and 10 mg of brompheniramine in the compartment, and 60 mg of pseudoephedrine and 6 mg of brompheniramine in the lamina; and (3) 90 mg of pseudoephedrine and 5 mg of brompheniramine in the compartment, and 30 mg of pseudoephedrine and 3 mg of brompheniramine in the lamina.

A representative example of a 240/16 dosage system, expressed in weight percent is as follows: a compartment weighing 260 mg comprising 69% pseudoephedrine hydrochloride, 3.8% brompheniramine maleate, 9.6% sodium chloride, 3% hydroxypropylmethylcellulose, 10% microcrystalline cellulose, 3% polyvinyl pyrrolidone, 1% magnesium stearate, and 0.5% silicon dioxide; a wall weighing 36.8 mg comprising 75% cellulose triacetate and 25% hydroxypropylcellulose; and, a lamina weighing 84.5% comprising 72.7% pseudoephedrine hydrochloride, 7.3% brompheniramine maleate, and 20% hydroxypropylmethylcellulose. The dosage form can comprise an additional outermost coat of hydroxypropylmethylcellulose to enhance its taste and to improve its appearance. The dosage form had four 0.5 mm passageways, and delivered its compartment pseudoephedrine hydrochloride in solution at approximately 10 mg/hr, and the brompheniramine maleate delivered in solution at the contracted rate of approximately 0.6 mg/hr.

Another representative example containing a total of 120 mg of pseudoephedrine and 8 mg brompheniramine of comprised the following: a compartment weighing 130 mg consisting essentially of 69.1% pseudoephedrine hydrochloride, 3.8% brompheniramine maleate, 9.6% sodium chloride, 3% hydroxypropylmethylcellulose, 10% microcrystalline cellulose, 3% polyvinyl pyrrolidone, 1% magnesium stearate, and 0.5% silicon dioxide; a wall weighing 21 mg comprising 75% cellulose triacetate and 25% hydroxypropylcellulose; and a lamina weighing 41.6 mg comprising 72.7% pseudoephedrine hydrochloride, 7.3% brompheniramine maleate and 20% hydroxypropylcellulose. The dosage form had two 0.5 mm passageways and dispensed the pseudoephedrine hydrochloride thorough the passageways in solution at a rate of about 5 mg/hr and dispensed the brompheniramine maleate in solution through the passageways at a rate of 0.3 mg/hr.

Plasma profiles determined by a computer simulated study using pharmacokinetic data and release rates from dosage forms of the invention indicated a dosage form index of 2.3 for pseudoephedrine and 1.7 for brompheniramine.

In summary, it will be appreciated that the present invention contributes to the art an unobvious dosage form that possesses practical utility. While the invention has been described and pointed out in detail with reference to operative embodiments thereof, it will be understood that those skilled in the art will appreciate that various changes, modifications, substitutions and omissions can be made without departing from the spirit of the invention. It is intended, therefore, that the invention embraces those equivalents within the scope of the claims which follow.

We claim:

1. A dosage form for delivering the beneficial drugs pseudoephedrine and brompheniramine to an environment of use, the dosage form comprising:
   (a) a wall comprising cellulose triacetate and hydroxypropylcellulose, which wall is permeable to the passage of fluid present in the environment, substantially impermeable to the passage of drug, and surrounds and defines;
   (b) a compartment;
   (c) a dosage amount of pseudoephedrine and brompheniramine in the compartment;
   (d) at least one passageway in the wall for connecting the compartment with the exterior of the dosage form;
   (e) a lamina comprising pseudoephedrine, brompheniramine and hydroxypropylmethylcellulose in laminar arrangement with the exterior of the wall; and,
   (f) wherein when the dosage form is in operation, the dosage form codelivers pseudoephedrine and brompheniramine at a ratio greater than their mutual equilibrium solubility in fluid that enters the dosage form.

2. A dosage form for delivering the beneficial drugs pseudoephedrine and brompheniramine to an environment of use, the dosage form comprising:
   (a) a wall comprising cellulose triacetate and hydroxypropylcellulose, which wall is permeable to the passage of fluid present in the environment of use, substantially impermeable to the passage of drug, and surrounds and defines:
   (b) a compartment;
   (c) a dosage amount of pseudoephedrine and brompheniramine in the compartment, said drugs present in a mass ratio of from 8:1 to 20:1;
   (d) at least one passageway in the wall for connecting the compartment with the exterior of the dosage form;
   (e) a lamina comprising pseudoephedrine, brompheniramine and hydroxyproplmethylcellulose in laminar arrangement with the exterior of the wall; and,
   (f) wherein when the dosage form is in operation, the dosage form codelivers pseudoephedrine and brompheniramine in a mass ratio of from 8:1 to 20:1 to the environment of use.

3. The dosage form for delivering the beneficial drugs to the environment of use according to claim 2, wherein pseudoephedrine is present as its pharmaceutically acceptable salt.

4. The dosage form for delivering the beneficial drugs to the environment of use according to claim 2, wherein brompheniramine is present as its pharmaceutically acceptable salt.

5. A dosage form for delivering the beneficial drugs pseudoephedrine and brompheniramine to a warm-blooded animal, wherein the dosage form comprises:
   (a) a wall comprising cellulose triacetate and hydroxypropylcellulose, which wall surrounds and forms;
   (b) a compartment;
   (c) a dosage amount of 170 to 200 mg of pseudoephedrine and 10 to 20 mg of brompheniramine in the compartment;
   (d) at least one passageway in the wall for connecting the compartment with the exterior of the dosage form;
   (e) a lamina comprising 55 to 65 mg of pseudoephedrine, 5 to 8 mg of brompheniramine and hydroxypropylmethylcellulose in lamina arrangement with the exterior of the wall; and,
   (f) wherein when the dosage form is in operation the dosage form codelivers from the compartment pseudoephedrine and brompheniramine in a mass ratio of 10:1 to 15:1 which ratio corresponds to their initial ratio in the compartment.

6. The dosage form for delivering the beneficial drugs according to claim 5, wherein the compartment comprises 180 mg of pseudoephedrine hydrochloride.

7. The dosage form for delivering the beneficial drugs according to claim 5 wherein the compartment comprises 10 mg of brompheniramine maleate.

8. The dosage form for delivering the beneficial drugs according to claim 5, wherein the lamina comprises 60 mg of pseudoephedrine hydrochloride.

9. The dosage form for delivering the beneficial drugs according to claim 5, wherein the lamina comprises 6 mg of brompheniramine maleate.

10. A dosage form for delivering the beneficial drugs pseudoephedrine and brompheniramine to a warm-blooded animal, wherein the dosage form comprises:
    (a) a wall comprising cellulose triacetate and hydroxypropylcellulose, which wall surrounds and defines;
    (b) a compartment;
    (c) a dosage amount of 80 to 110 mg of pseudoephedrine and 3 to 8 mg of brompheniramine in the compartment;
    (d) at least one passageway in the wall for communicating the exterior of the dosage form with the compartment;
    (e) a lamina comprising 25 to 35 mg of pseudoephedrine, 2 to 5 mg of brompheniramine and hydroxypropylmethylcellulose coated onto the exterior surface of the wall; and,
    (f) wherein when the dosage form is in the animal, the dosage form codelivers from the compartment pseudoephedrine and brompheniramine in a mass ratio of 10:1 to 15:1 which corresponds to their initial ratio in the compartment.

11. The dosage form for delivering the beneficial drugs according to claim 10, wherein the compartment comprises 90 mg of pseudoephedrine hydrochloride.

12. The dosage form for delivering the beneficial drugs according to claim 10, wherein the compartment comprises 3 mg of brompheniramine maleate.

13. The dosage form for delivering the beneficial drugs according to claim 10, wherein the lamina comprises 30 mg of pseudoephedrine hydrochloride.

14. The dosage form for delivering the beneficial drugs according to claim 10, wherein the lamina comprises 3 mg of brompheniramine maleate.

* * * * *